United States Patent
Baumgartner et al.

(10) Patent No.: US 12,077,655 B2
(45) Date of Patent: Sep. 3, 2024

(54) TERMINAL ALKENYL FUNCTIONAL SILYLATED POLYSACCHARIDES

(71) Applicants: Dow Silicones Corporation, Midland, MI (US); Rohm and Haas Company, Collegeville, PA (US)

(72) Inventors: Ryan Baumgartner, Midland, MI (US); Shane Mangold, Midland, MI (US); Zachary Wenzlick, Midland, MI (US); Marc-Andre Courtemanche, Midland, MI (US); Michael Ferritto, Midland, MI (US); Gregoire Cardoen, Collegeville, PA (US)

(73) Assignees: Dow Silicones Corporation, Midland, MI (US); Rohm and Haas Company, Collegeville, PA (US)

(*) Notice: Subject to any disclaimer, the term of this patent is extended or adjusted under 35 U.S.C. 154(b) by 0 days.

(21) Appl. No.: 18/261,177

(22) PCT Filed: Feb. 24, 2022

(86) PCT No.: PCT/US2022/017665
§ 371 (c)(1),
(2) Date: Jul. 12, 2023

(87) PCT Pub. No.: WO2022/203799
PCT Pub. Date: Sep. 29, 2022

(65) Prior Publication Data
US 2024/0262987 A1     Aug. 8, 2024

Related U.S. Application Data

(60) Provisional application No. 63/163,968, filed on Mar. 22, 2021.

(51) Int. Cl.
| | | |
|---|---|---|
| C08L 1/08 | (2006.01) |
| C07H 1/00 | (2006.01) |
| C07H 23/00 | (2006.01) |
| C08B 15/05 | (2006.01) |
| C08B 30/18 | (2006.01) |
| C08B 31/00 | (2006.01) |
| C08B 37/00 | (2006.01) |
| C08B 37/02 | (2006.01) |
| C08L 3/02 | (2006.01) |
| C08L 3/04 | (2006.01) |
| C08L 5/02 | (2006.01) |
| C08L 5/08 | (2006.01) |
| C08L 5/12 | (2006.01) |
| C08L 5/16 | (2006.01) |

(52) U.S. Cl.
CPC .......... *C08L 1/08* (2013.01); *C07H 1/00* (2013.01); *C07H 23/00* (2013.01); *C08B 15/05* (2013.01); *C08B 30/18* (2013.01); *C08B 31/00* (2013.01); *C08B 37/0018* (2013.01); *C08B 37/0021* (2013.01); *C08B 37/0039* (2013.01); *C08B 37/0054* (2013.01); *C08B 37/0063* (2013.01); *C08B 37/0087* (2013.01); *C08L 3/02* (2013.01); *C08L 3/04* (2013.01); *C08L 5/02* (2013.01); *C08L 5/08* (2013.01); *C08L 5/12* (2013.01); *C08L 5/16* (2013.01)

(58) Field of Classification Search
None
See application file for complete search history.

(56) References Cited

U.S. PATENT DOCUMENTS

| | | |
|---|---|---|
| 5,025,073 A | 6/1991 | Lewis et al. |
| 5,403,898 A | 4/1995 | Bradshaw et al. |
| 5,498,703 A | 3/1996 | O'Lenick, Jr. |
| 6,372,020 B2 | 4/2002 | Hong et al. |
| 6,703,497 B1 | 3/2004 | Ladouce et al. |
| 7,235,186 B2 | 6/2007 | Ochs et al. |
| 10,053,543 B2 | 8/2018 | Knoer |
| 2018/0282438 A1 | 10/2018 | Mukai et al. |

FOREIGN PATENT DOCUMENTS

| | | |
|---|---|---|
| CN | 107880089 | 4/2018 |
| EP | 2727923 | 5/2014 |
| JP | 5528648 | 6/2014 |
| WO | 2014182907 | 11/2014 |

(Continued)

OTHER PUBLICATIONS

Synthesis and characterization of persilylated cyclodextrins, Carbohydrate Polymers 56, (2004), 301-311, Harabagiu et al. (Year: 2004).*
Google scholar search (polysaccharide and divinyl disilazane) (Year: 2024).*
Google scholar search (cyclodextrin and divinyl disilazane) (Year: 2024).*
Fischer, Permethyl-B-cyclodextrin, Chemically Bonded to Polysiloxane: a Chrial Stationary Phase with Wider Application Range for Enantiomer Separation by Capillary Gas Chromatography, Angew. Chem. Int. Ed. Engl., 1990, vol. 29, No. 4, pp. 427-429.

(Continued)

*Primary Examiner* — Peter A Salamon
(74) *Attorney, Agent, or Firm* — Steven W. Mork

(57) ABSTRACT

A composition contains a silylated polysaccharide, where the silylated polysaccharide is characterized by: (a) having linked fructose, galactose, anhydrogalactose, or glucose saccharide units provided that glycosidic linkages of glucose are alpha linkages and that the silylated polysaccharide is other than a silylated starch; and (b) on average 1 to 100 mole-percent of the hydroxyl groups on the polysaccharide have been silylated with a silyl group having the structure —SiR$_3$ linked to the polysaccharide through a C—O—Si bond where each R is independently selected from hydrocarbyl radicals having from one to 12 carbon atoms, provided that on average at least one R per polysaccharide has a terminally unsaturated carbon-carbon double bond.

10 Claims, No Drawings

(56) References Cited

FOREIGN PATENT DOCUMENTS

| WO | 2020139403 | 7/2020 |
|----|------------|--------|
| WO | 2020139404 | 7/2020 |

OTHER PUBLICATIONS

Harabagiu, "Synthesis and characterization of persilylated cyclodextrins", Carbohydrate Polymers, 2004, vol. 56, iss. 3, pp. 301-311.

Stiubianu, "Chemical modification of cellulose acetate by allylation and crosslinking with siloxane derivatives", Polym. Int., 2012, vol. 61, pp. 1115-1126.

Tingaut, "Highly efficient and straightforward functionalization of cellulose films with thiol-ene click chemistry", Journal of Materials Chemistry, 2011, vol. 21, No. 40, p. 16066.

Wenke, "Assembly, structure, and properties of cross-linked polymer structures from lipophilic cyclodextrin derivatives", Ph.D. Dissertation, 1993.

\* cited by examiner

TERMINAL ALKENYL FUNCTIONAL SILYLATED POLYSACCHARIDES

FIELD OF THE INVENTION

The present invention relates to a terminal alkenyl functional silylated polysaccharide that links the alkenyl group to the polysaccharide through a C—O—Si linkage.

INTRODUCTION

Bio-renewable and/or bio-sourced materials are desirable for many uses, including for use in the cosmetic industry. Silicone elastomer materials have been desirable in the cosmetic industry to impart desirable sensory properties to cosmetics, especially in the area of feel and touch on skin-based cosmetics. Combining a bio-renewable and/or bio-sourced aspect to silicone elastomer materials for cosmetics would be one way to advance the field of cosmetics.

Polysaccharides are a bio-renewable and bio-sourced materials. In order to incorporate them into silicone elastomer materials it is necessary to functionalize the polysaccharides with a reactive group enabling it to be incorporated into silicone elastomer molecules. For instance, it is desirable to obtain a polysaccharide functionalized with an alkenyl group having a terminal carbon-carbon double bond (C═C), such as a vinyl group, that can undergo further reactions such as hydrosilylation to form a silicone elastomer.

A challenge, however, is achieving desirable properties in such a functionalized polysaccharide.

It is desirable to have a polysaccharide functionalized with a terminal alkenyl group having a terminal C═C and that is linked to the saccharide unit through a carbon-oxygen-silicon (C—O—Si) bond linkage rather than a carbon-oxygen-carbon (C—O—C) bond linkage. C—O—Si linkages are less hydrolytically stable than C—O—C linkage, which renders molecules with C—O—Si linkages more degradable and environmentally friendly. Additionally, alkoxylated materials with C—O—C bond linkages can carry with them trace level of 1,4-dioxane, which is an undesirable contaminate particularly in a cosmetic material.

It is also desirable to identify a polysaccharide functionalized with an alkenyl group having a terminal C═C that is soluble in a non-polar aromatic organic solvent such as benzene in order to facilitate its use in reactions conducted in non-polar organic solvents.

It is further desirable to identify a polysaccharide functionalized with an alkenyl group having a terminal C═C that is capable of undergoing hydrosilylation with an Si—H functional material using a platinum catalyst to form a gel while still achieving a low coloration (less than 300 on the APHA scale as determined by ASTM D1209-05). A common challenge with hydrosilylation reaction is that the platinum catalyst can result in yellowing, even to the point of turning the reaction product amber or brown. Such discoloration is undesirable in cosmetic applications.

BRIEF SUMMARY OF THE INVENTION

The present invention provides a polysaccharide functionalized with an alkenyl group having a terminal C═C that achieves one or more than one of the aforementioned desirable characteristics. The present invention provides a polysaccharide functionalized with a terminal alkenyl group having a terminal C═C that is linked to a saccharide unit through a C—O—Si bond linkage. The present invention provides a polysaccharide functionalized with an alkenyl group having a terminal C═C that is soluble in non-polar organic solvent such as benzene. Moreover, the present invention provides a polysaccharide functionalized with an alkenyl group having a terminal C═C can undergo hydrosilylation with an Si—H functional material using a platinum catalyst while still achieving a low coloration (less than 300 on the APHA scale as determined by ASTM D1209-05).

The present invention is a result of surprisingly combining a silylation reaction with polysaccharides to obtain a polysaccharide functionalized with an alkenyl group having a terminal C═C with a C—O—Si linkage between the saccharide unit and the alkenyl group and further identifying which polysaccharides and what extent of functionalization is required to achieve such a functionalized polysaccharide that is soluble in non-polar aromatic hydrocarbon solvents such as benzene. It is yet more a surprising discovery to find such a functionalized polysaccharide that can undergo hydrosilylation using a platinum catalyst while still achieving low coloration.

In a first aspect the present invention is a composition comprising a silylated polysaccharide, where the silylated polysaccharide is characterized by: (a) comprising linked fructose, galactose, anhydrogalactose, or glucose saccharide units provided that glycosidic linkages of glucose are alpha linkages and that the silylated polysaccharide is other than a silylated starch; and (b) on average 1 to 100 mole-percent of the hydroxyl groups on the polysaccharide have been silylated with a silyl group having the structure —SiR$_3$ linked to the polysaccharide through a C—O—Si bond where each R is independently selected from hydrocarbyl radicals having from one to 12 carbon atoms, provided that on average at least one R per polysaccharide has a terminally unsaturated carbon-carbon double bond.

In a second aspect the present invention is a method for preparing the silylated polysaccharide of the first aspect, the method comprising the steps: (a) providing a polysaccharide comprising fructose, galactose, anhydrogalactose, or glucose linked saccharide units provided that glycosidic linkages of glucose are alpha linkages and that the silylated polysaccharide is other than a silylated starch; (b) silylating on average 1 to 100 mole-percent of the hydroxyl groups on the polysaccharide by substituting the hydrogen atom of the hydroxyl group with a group having the formula: —SiR$_3$ where R is independently selected from hydrocarbyl radicals having from one to 12 carbon atoms, provided that on average at least one R per polysaccharide has a terminally unsaturated carbon-carbon double bond.

Surprisingly, the silylated polysaccharides of the present invention are soluble in non-polar aromatic solvents such as benzene. Silylated starch is expressly excluded from the scope of the present invention because it is not soluble in non-polar aromatic solvents such as benzene as evident in the samples of the Examples sections herein below.

The process of the present invention is useful for preparing the polysaccharide functionalized with an alkenyl group having a terminal C═C of the present invention, which is useful for use in synthetic processes for making polysiloxane gels having bio-renewable and/or bio-sourced characteristics.

DETAILED DESCRIPTION OF THE INVENTION

Test methods refer to the most recent test method as of the priority date of this document when a date is not indicated with the test method number. References to test methods contain both a reference to the testing society and the test method number. The following test method abbreviations and identifiers apply herein: ASTM refers to ASTM International methods; END refers to European Norm; DIN refers to Deutsches Institut für Normung; ISO refers to International Organization for Standards; and UL refers to Underwriters Laboratory.

Products identified by their tradename refer to the compositions available under those tradenames on the priority date of this document.

"Multiple" means two or more. "And/or" means "and, or as an alternative". All ranges include endpoints unless otherwise indicated.

"Hydrocarbyl" refers to a univalent group formed by removing a hydrogen atom from a hydrocarbon and includes alkyl and aryl groups.

"Alkyl" refers to a hydrocarbon radical derivable from an alkane by removal of a hydrogen atom. An alkyl can be linear or branched.

"Aryl" refers to a radical formable by removing a hydrogen atom from an aromatic hydrocarbon.

"Polysaccharide" refers to a molecule comprising 2 or more saccharide units that are covalently bonded together. "Polysaccharide" includes what is sometimes referred to as a "disaccharide" and "oligosaccharide". A "disaccharide" is a molecule comprising 2 saccharide units that are covalently bonded together. An "oligosaccharide" is a molecule comprising from 3 to 10 saccharide units covalently bonded in a chain, which can be a cyclical chain.

"Pendant groups", with respect to polysaccharides, refer to groups other than hydrogen extending off from a polysaccharide backbone, specifically from a carbon atom on a pyranose or furanose ring of a polysaccharide backbone. Adjoining saccharide groups in a polysaccharide are not considered "pendant groups" but rather part of the polysaccharide backbone.

"Starch" refers to a combination of amylose and amylopectin.

"APHA" refers to American Public Health Association.

"Terminal alkenyl" refers to a univalent aliphatic hydrocarbon radical derivable from an alkene having a carbon-carbon double bond (C=C) where a carbon atom of the C=C is a terminal carbon and where the univalent aliphatic hydrocarbon radical is derivable by removing one hydrogen atom from a carbon atom other than the terminal carbon atom in the C=C.

The present invention is a composition comprising, and can consist of, a silylated polysaccharide. The silylated polysaccharide is characterized by at least the following characteristics:

(a) The silylated polysaccharide comprises linked fructose, galactose, anhydrogalactose or glucose saccharide units, provided that glycosidic linkages of glucose saccharide units are alpha linkages. Alpha glycosidic linkages are those occurring where the C1 and C4 carbons have the same stereochemistry. In contrast, beta glycosidic linkages are those occurring when the C1 and C4 carbons have different stereochemistry.

The silylated polysaccharide is also characterized by being other than silylated starch. That is, the silylated polysaccharide is not starch. Interestingly, silylated starch has been found to be insoluble in non-polar aromatic solvents such as benzene while similar silylated polysaccharides that are in scope of the present invention are soluble in non-polar aromatic solvents.

(b) On average, one mole-percent (mol %) or more, preferably 3 mol % or more, 5 mol % or more, 10 mol % or more, 15 mol % or more, 20 mol % or more, mol % or more, 30 mol % or more, 33 mol % or more, 40 mol % or more, 45 mol % or more, 50 mol % or more, 55 mol % or more, 60 mol % or more, 65 mol % or more, 70 mol % or more, 75 mol % or more, 80 mol % or more, 85 mol % or more, even 90 mol % or more, 95 mol % or more while at the same time 100 mol % or fewer, and possibly 95 mol % or fewer, 90 mol % or fewer, 85 mol % or fewer, 80 mol % or fewer, 75 mol % or fewer, 70 mol % or fewer, 65 mol % or fewer, 60 mol % or fewer, 55 mol % or fewer, even 50 mol % or fewer of the hydroxyl groups on the polysaccharide have been silylated with a silyl group having the structure —SiR$_3$. For avoidance of doubt, the polysaccharide typically comprises a multitude of polysaccharide molecules and on average the mole-percent hydroxyl groups is per polysaccharide molecule. Each R of the —SiR$_3$ groups is independently selected from hydrocarbyl radicals having one or more, 2 or more 3 or more, 4 or more, 5 or more, even 6 or more while at the same time 12 or fewer, 10 or fewer, 8 or fewer, even 6 or fewer, or 4 or fewer carbon atoms. At least one, preferably two or more, R group per silylated polysaccharide has a terminally unsaturated carbon-carbon double bond (C=C). "Terminally unsaturated" means that there is a C=C between two carbons most remote from the silicon atom of the —SiR$_3$ group along a continuous carbon chain. Desirably, the R groups are selected from methyl and vinyl groups. Preferably, the R group having terminally unsaturated C=C is a vinyl group because vinyl groups do not undergo isomerization like longer chain terminally unsaturated alkyl groups (such as allyl). Isomerization is particularly undesirable because isomerization products can break down to form acetaldehyde, which contributes to undesirable odor.

The —SiR$_3$ group is linked to the polysaccharide through a C—O—Si bond. The carbon of the C—O—Si bond is preferably a carbon of the hexose of a polysaccharide unit to which the —SiR$_3$ group is attached. The silicon atom of the C—O—Si bond can be the silicon atom of a —SiR$_3$ group or a silicon atom in a polysiloxane to which the —SiR$_3$ group is attached.

Determine extent of hydroxyl silylation and extent of alkenyl substitution by proton nuclear magnetic resonance spectroscopy ($^1$H NMR). For example, dissolve a 10-milligram sample in 0.6 milliliters of d6-benzene and analyze by $^1$H NMR in a 400 MHz Varian NMR spectrometer. Use a 5 second acquisition time and a relaxation delay time of 15 seconds and collect 16 scans. Reference final spectra to residual benzene at δ 7.16 ppm. Regions for the particular groups in the spectra are: unsaturated region ("U") integrated over δ 5.6-6.5 ppm to account for either: all 3 protons of vinyl groups ("U"="A") or 1 proton of other terminal alkenyl groups (3"U"="A"), saccharide region ("S") is integrated over δ 3.6-4.6 ppm, and methyl region ("M") is integrated over δ 0.20-0.55 ppm. Normalize the saccharide region to methanediyl and methanetriyl hydrogens excluding the anomeric carbon hydrogen.

Determine the following sample attributes according to their associated calculations:

Mole-percent (Mol %) —OH substitution={[(A/3)+(M-2*A)]/[—OH per starting saccharide]}*100%

This value corresponds to the mol % of hydroxyl groups on the polysaccharide that have been silylated with and —SiR$_3$ linked to the polysaccharide through a C—O—Si bond.

Mol % terminal alkenyl substitution (Mol % Alkenyl)=[(A/3)]/[(A/3)+(M-2*A)]*100%

Terminal alkenyl groups per polysaccharide=[(Mol % Alkenyl)]*[Mol % —OH substitution]*[—OH per starting saccharide]*[Degree of Polymerization]/10$^4$ where:

"[—OH per starting saccharide]" values are 2 for agarose, 4 for disaccharides and 3 for all other polysaccharides in scope of the present invention "Degree of Polymerization" ("DP") refers to the number of polysaccharide units per polysaccharide molecule and can be obtained from the supplier of the polysaccharide or by determined using routine GPC methods.

For samples in the Experimental section that are insoluble in d6-benzene, determine Mol % —OH substitution by neutron activation analysis (NAA). Prepare duplicate analyte materials by transferring 1.0 grams of sample into pre-cleaned 2-dram polyethylene vials. Prepare silicon standard aliquots from NIST traceable standard solutions by taking appropriate amounts into similar vials to the samples. Dilute to the same volumes as the analyte materials using pure water. Also prepare a blank containing only pure water. Analyze the analyte materials, standards and blank following standard NAA procedure—irradiating for 2 minutes at 100 kW. After a waiting time of 9 minutes, carry out gamma ray spectroscopy using high purity germanium detectors. Determine silicon concentrations (wt % Si) using standard comparative technique with CANBERRA software. Calculate the mol % —OH substitution using the following calculations:

Mol % —OH substitution=([MW of starting polysaccharide repeat unit]*[wt % Si])/{(28-84*[wt % Si]/100)*[—OH per starting saccharide]}. This corresponds to the mol % of hydroxyl groups on the polysaccharide that have been silylated with and —SiR$_3$ linked to the polysaccharide through a C—O—Si bond. [MW of repeating polysaccharide repeat unit] is 154 for agarose, 171 for disaccharides and 162 for all other polysaccharides in scope of the present invention. [—OH per starting saccharide] is 2 for agarose, 4 for disaccharides and 3 for all other polysaccharides.

Typically, the silylated polysaccharide can be further characterized by having pendant groups on the polysaccharide backbone that are selected from a group consisting of —OH, —CH$_2$OH, —OSiR$_3$ and —CH$_2$OSiR$_3$ where the —SiR$_3$ silyl group is linked to the polysaccharide backbone through a C—O—Si linkage.

The silylated polysaccharide is desirably selected from a group consisting of silylated beta-cyclodextrin, silylated maltodextrin, silylated pullulan, silylated dextran, silylated trehalose, silylated sucrose, silylated lactose, silylated maltose, silylated inulin, silylated agarose, alpha-cyclodextrin, and gamma-cyclodextrin. Preferably, the silylated polysaccharide is a silylated beta-cyclodextrin. In exploring the polysaccharides of the present invention, the inventors discovered that silylated beta-cyclodextrin has particularly surprising and beneficial properties. For instance, silylated beta-cyclodextrin of the present invention can be used in subsequent hydrosilylation reactions without experiencing significant coloration (that is, without exceeding 300 on the APHA scale as determined by ASTM D1209-05), while most other silylated polysaccharides result in a greater extent of coloration during subsequent hydrosilylation reaction. Low color formation is desirable particularly for making polysiloxane elastomers for use in cosmetics.

The silylated polysaccharide (and the pre-silylated polysaccharide used to make the silylated polysaccharide) desirably contains on average from 2 to 2000 saccharide units per molecule. Typically, the polysaccharide has an average DP (average number of polysaccharides units per molecule) of 2 or more, 3 or more, 4 or more, 5 or more, 6 or more, 7 or more, 8 or more, 9 or more, 10 or more, 20 or more, 40 or more, 60 or more, 80 or more, even 100 or more, or 200 or more while at the same time typically comprise 2000 or fewer, 1800 or fewer, 1600 or fewer, 1400 or fewer, 1200 or fewer, 1000 or fewer, 800 or fewer, 600 or fewer, 400 or fewer, 200 or fewer, 100 or fewer, 80 or fewer, 60 or fewer, 40 or fewer, 20 or fewer, 10 or fewer, even 8 or fewer, or even 7 or fewer or 6 or fewer. Determine the average DP by routine Gel Permeation Chromatography (GPC) methods.

The composition of the present invention can consist of the silylated polysaccharide or comprise the silylated polysaccharide and other components. For instance, the composition can comprise the silylated polysaccharide in combination with polysaccharides and/or polysiloxanes other than the silylated polysaccharide.

Prepare the silylated polysaccharides of the present invention by first providing a polysaccharide comprising fructose, galactose, anhydrogalactose, or glucose linked saccharide units provided that glycosidic linkages of glucose are alpha linkages and that the polysaccharide is other than a starch; then silylate on average one mole-percent (mol %) or more, preferably 3 mol % or more, 5 mol % or more, 10 mol % or more, 15 mol % or more, mol % or more, 25 mol % or more, 30 mol % or more, 33 mol % or more, 40 mol % or more, 45 mol % or more, 50 mol % or more, 55 mol % or more, 60 mol % or more, 65 mol % or more, 70 mol % or more, 75 mol % or more, 80 mol % or more, 85 mol % or more, even 90 mol % or more, 95 mol % or more while at the same time 100 mol % or fewer, and possibly 95 mol % or fewer, 90 mol % or fewer, 85 mol % or fewer, 80 mol % or fewer, 75 mol % or fewer, 70 mol % or fewer, 65 mol % or fewer, 60 mol % or fewer, 55 mol % or fewer, even 50 mol % or fewer of the hydroxyl groups on the polysaccharide a silyl group having the structure —SiR$_3$. Each R of the —SiR$_3$ groups is independently selected from hydrocarbyl radicals having one or more, 2 or more 3 or more, 4 or more, 5 or more, even 6 or more while at the same time 12 or fewer, 10 or fewer, 8 or fewer, even 6 or fewer, or 4 or fewer carbon atoms. At least one, preferably two or more, R group per silylated polysaccharide has a terminally unsaturated carbon-carbon double bond (C=C). Desirably, the R groups are selected from methyl and vinyl groups.

For avoidance of doubt, the polysaccharide typically comprises a multitude of polysaccharide molecules and on average the mole-percent hydroxyl groups is per polysaccharide molecule.

Silylate the polysaccharide using a silylation reaction. The silylation reaction typically comprises combining a polysaccharide and a silylating agent together and then heating while stirring. A catalyst can also be used to aid in the silylation reaction. The concentration of polysaccharide and silylating agent is selected to achieve a desired level of polysaccharide hydroxyl group silylation.

The polysaccharide is desirably selected from a group consisting of beta-cyclodextrin, maltodextrin, pullulan, dextran, trehalose, inulin, and agarose so that the silylation reaction produces a silylated polysaccharide selected from a group consisting of silylated beta-cyclodextrin, silylated maltodextrin, silylated pullulan, silylated dextran, silylated trehalose, silylated inulin, and silylated agarose. Preferably, dry the polysaccharide prior to the silylation reaction for example by subjecting it to vacuum at 90° C. for 24 hours.

The silylating agent can be any material that is capable of silylating hydroxyl groups with the previously described —$SiR_3$ functionality. Typically, the silylating agent is selected from a silazane, silane, alkoxysilane, siloxane, chlorosilane, silylamide, silylcarbamate, silyl azide, silylacetate, silyl cyanide, silthiane, silyl thioacetate, silyl sulfonate, silyl urea or any combination thereof. Preferably, the silylating agent is a silazane such as 1,1,3,3-tetramethyl-1,3-divinyldisilazane alone or in combination with hexamethyldisilazane.

The reaction can occur in the presence or absence of a solvent in addition to the polysaccharide and silylating agent. When using a solvent, add the polysaccharide and silylating agent together in the solvent and mix while heating. Examples of suitable solvents include N,N-dimethylacetamide (DMAc), dimethylsulfoxide (DMSO), N,N-dimethylformamide (DMF), N-methylpyrrolidone, isododecane (IDD), farnesane, xylenes, toluene, and ethyl acetate. Notably, the reaction can be carried out in an absence of polar aprotic solvents. Moreover, the reaction can be carried out in an absence of solvent altogether, particularly for polysaccharides with an average DP of 8 or less, such as beta-cyclodextrin and maltodextrin.

The silylation reaction can occur in the presence of or absence of a catalyst in addition to the polysaccharide and silylating agent and, optionally, solvent. The catalyst can generally be an acid, Lewis acid, base or Lewis base. Examples of suitable catalysts include saccharin, imidazole, ammonium chloride, trifluoroacetic acid and ammonium sulfate.

Examples

Table 1 lists the materials for use in the following samples.

TABLE 1

| Material | Description | Source |
|---|---|---|
| Solvent 1 | Dimethylacetamide | Sigma-Aldrich |
| Solvent 2 | Isododecane | PUROLAN ™ IDD from LANXESS |
| Solvent 3 | Farnesane | Available as NEOSSANCE ™ Hemisqualane from Aprinnova |
| Solvent 4 | Xylenes | Sigma-Aldrich |
| Solvent 5 | Toluene | Sigma-Aldrich |
| Solvent 6 | Ethyl acetate | Sigma-Aldrich |
| Polysaccharide 1 | Beta-cyclodextrin | Oakwood Chemical |
| Polysaccharide 2 | Maltodextrin Dextrose Equivalent = 6.5 | MALTRIN ™ 040 from Grain Processing Corporation. |
| Polysaccharide 3 | Maltodextrin Dextrose Equivalent = 24.1 | MALTRIN ™ 250 from Grain Processing Corporation. |
| Polysaccharide 4 | Rice Starch | Sigma-Aldrich (catalog #S7260) |
| Polysaccharide 5 | Dextran (150,000 Daltons) | Sigma-Aldrich |
| Polysaccharide 6 | Inulin | Sigma-Aldrich (catalog #12255) |
| Polysaccharide 7 | Pullulan | TCI (catalog #P0978) |
| Polysaccharide 8 | Chitin | TCI (catalog #C0072) |
| Polysaccharide 9 | Xanthan Gum | TCI (catalog #X0048) |
| Polysaccharide 10 | Cellulose (from Eucalyptus pulp), approximately 2500 saccharide units | Crystal PL HD from Bahia Specialty Cellulose |
| Polysaccharide 11 | Trehalose Dihydrate | Sigma-Aldrich (catalog #T5251) |
| Polysaccharide 12 | Agarose, type I, Low EEO | Sigma-Aldrich (catalog #A6013) |
| Polysaccharide 13 | Maltodextrin Dextrose Equivalent = 4-7 | Sigma-Aldrich (catalog #419672) |
| Polysaccharide 14 | Maltodextrin Dextrose Equivalent = 15.0 | Available under the name MALTRIN ™ 150 from Grain Processing Corporation. |
| Polysaccharide 15 | Methyl beta-cyclodextrin | Alfa Aesar (catalog #J66847) |
| Silazane 1 | Hexamethyldisilazane | Sigma-Aldrich |
| Silazane 2 | 1,1,3,3-tetramethyl-1,3-divinyldisilazane | Gelest (catalog #SD4612.0) |
| Catalyst 1 | Saccharin | Sigma-Aldrich |
| Catalyst 2 | Imidazole | Sigma-Aldrich |
| Catalyst 3 | Ammonium Chloride | Sigma-Aldrich |
| Catalyst 4 | Ammonium Sulfate | Sigma-Aldrich |
| Catalyst 5 | Trifluoroacetic Acid | Sigma-Aldrich |
| Platinum Catalyst | Platinum-based catalyst | SYL-OFF ™ 4000 catalyst |
| SiH Polymer | H—[$(CH_3)_2SiO]_{16.5}$—$Si(CH_3)_2$H | Synthesis according to teachings in U.S. Pat. No. 4,370,358 (see, columns 4-5). |

PUROLAN is a trademark of LANXESS Distribution GmbH. MALTRIN is a trademark of Grain Processing Corporation. SYL-OFF is a trademark of The Dow Chemical Company. NEOSSANCE is a trademark of Amyris, Inc.

Sample Preparation

Prepare the samples in the following manner using the formulation in Table 2. For those samples indicating the polysaccharide was dried, dry the polysaccharide prior to the reaction in vacuum (1.3 kilo Pascals, 10 mm Hg) at 90 degrees Celsius (° C.) for 24 hours. Add the specified amount of polysaccharide, silazane, catalyst and solvent to a 40-milliliter vial. Add a polytetrafluoroethylene stir bar and inert the vial by purging with nitrogen gas and sealing with a septum. Place the vial on a heating block and heat to the stated temperature for the stated period while stirring.

Then allow the sample to cool and dry for 24 hours under vacuum (1.3 kiloPascals, 10 mm Hg) to yield the silylated polysaccharide sample.

Table 2 presents formulations for the silylated polysaccharide samples. The amount of polysaccharide is provided in grams (g). The amount of catalyst and amount of silazane are each presented in moles per mole of saccharide units in the specified grams of polysaccharide ("equiv"). The solvent concentration is present in molar concentration of the specified amount of polysaccharide in the combined volume of solvent and silazane ("M").

units with glycosidic linkages of glucose are alpha linkages all successfully silylated with ranges from 3 to 100 mol % of the saccharide hydroxyls being silylated.

Table 2 also reveals that a variety of different catalysts and even no catalyst at all can be successfully used in the silylation reaction.

Table 2 reveals that silylation reactions of polysaccharides with an average DP less than or equal to 8 (such as beta-cyclodextrin maltodextrin), and preferably that has a DP in a range of 4 to 8, can be successfully run to at least

TABLE 2

| Sample | Polysaccharide (g) | Catalyst (equiv) | Solvent (M) | Silazane (equiv) | Temp (° C.) | Time (hours) | Mol % OH Substitution | Mol % vinyl | Vinyl Functionality per Polysaccharide | Silylation Successful? (Y/N) |
|---|---|---|---|---|---|---|---|---|---|---|
| 1 | 1 (1.0) | None | 1 (0.6) | 1 (4) | 110 | 24 | 80.0 | 0 | 0 | Y |
| 2 | 1 (1.0) | 2 (0.1) | 4 (1.7) | 1 (2) | 110 | 6 | 66.7 | 0 | 0 | Y |
| 3 | 1 (1.0) | 4 (0.1) | 1 (1.7) | 1 (2) | 110 | 5 | 63.3 | 0 | 0 | Y |
| 4 | 1 (1.0) | 3 (0.1) | 1 (1.7) | 1 (2) | 110 | 6 | 53.3 | 0 | 0 | Y |
| 5 | 1 (1.0) | None | 1 (0.6) | 2 (4) | 110 | 18 | 76.7 | 100 | 16 | Y |
| 6 | 1 (1.0) | None | 1 (1.0) | 2 (1) | 110 | 24 | 3.3 | 100 | 0.7 | Y |
| 7 | 1 (1.0) | None | 1 (0.9) | 2 (1.5) | 110 | 24 | 13.3 | 100 | 2.8 | Y |
| 8 | 1 (1.0) | None | 1 (0.75) | 2 (2.5) | 110 | 8 | 36.7 | 100 | 7.7 | Y |
| 9 | 1 (50.0) | 1 (0.003) | None (3.2) | 1 (2) + 2 (0.35) | 100 | 8 | 70.0 | 6 | 0.9 | Y |
| 10 | 1* (1.0) | 1 (0.005) | 2 (0.9) | 1 (1.5) | 110 | 6 | 63.3 | 0 | 0 | Y |
| 11 | 1* (50.0) | 1 (0.003) | 1 (2.5) | 1 (1.35) + 2 (0.15) | 110 | 3 | 76.7 | 10 | 1.6 | Y |
| 12 | 1* (50.0) | 1 (0.006) | 1 (2.1) | 1 (1.25) + 2 (0.25) | 110 | 3 | 76.7 | 15 | 2.4 | Y |
| 13 | 1* (50.0) | 1 (0.001) | 1 (2.4) | 1 (1.25) + 2 (0.25) | 100 | 2 | 66.7 | 19 | 2.7 | Y |
| 14 | 1* (50.0) | 1 (0.003) | 1 (2.5) | 1 (1.15) + 2 (0.35) | 110 | 3 | 73.3 | 23 | 3.5 | Y |
| 15 | 1* (50.0) | 1 (0.001) | 3 (1.2) | 1 (1.15) + 2 (0.35) | 110 | 9 | 66.7 | 9 | 1.3 | Y |
| 16 | 1* (1.0) | 1 (0.001) | None (3.2) | 1 (1.0) + 2 (0.5) | 70-110 | 12 | 56.7 | 40 | 4.8 | Y |
| 17 | 1* (50.0) | 1 (0.0005) | 1 (2.4) | 1 (1.0) + 2 (0.5) | 100 | 2 | 70.0 | 33 | 4.9 | Y |
| 18 | 1* (1.0) | 1 (0.003) | None (2.4) | 2 (2) | 70 | 6 | 75 | 100 | 15.8 | Y |
| 19 | 13*(1.0) | 1 (0.003) | 2 (1.7) | 2 (2) | 70 | 6 | 23.3 | 100 | 14.1 | Y |
| 20 | 3 (10.0) | 1 (0.003) | 1 (1.8) | 1 (1.48) + 2 (0.63) | 70 | 15 | 76.7 | 40 | 4.1 | Y |
| 21 | 2* (1.0) | 1 (0.003) | None (2.4) | 2 (2) | 70 | 6 | 0.0 | 0 | 0 | N |
| 22 | 2* (1.0) | 1 (0.003) | 1 (1.7) | 2 (2) | 70 | 6 | 100.0 | 100 | 51 | Y |
| 23 | 2* (1.0) | 1 (0.003) | 1 (1.8) | 1 (1.45) + 2 (0.05) | 70 | 5 | 80.0 | 8 | 3.3 | Y |
| 24 | 3* (1.0) | 1 (0.003) | 1 (2.1) | 1 (1.25) + 2 (0.25) | 110 | 1 | 90.0 | 21 | 2.6 | Y |
| 25 | 3* (1.0) | 1 (0.003) | 1 (1.8) | 2 (1.5) | 70 | 5 | 80.0 | 100 | 10.8 | Y |
| 26 | 7* (1.0) | 1 (0.003) | 1 (1.8) | 2 (1.5) | 70 | 3 | 80.0 | 100 | 4440 | Y |
| 27 | 7* (1.0) | 1 (0.003) | 1 (2.1) | 1 (1.47) + 2 (0.03) | 110 | 3 | 80.0 | 3 | 133 | Y |
| 28 | 5* (1.0) | 1 (0.003) | 1 (2.1) | 2 (1.5) | 110 | 6 | 83.3 | 100 | 2315 | Y |
| 29 | 5* (1.0) | 1 (0.003) | 1 (2.1) | 1 (1.46) + 2 (0.04) | 70 | 2.5 | 76.7 | 4 | 85 | Y |
| 30 | 11 (1.0) | 1 (0.005) | 1 (2.1) | 2 (1.5) | 110 | 4 | 90.0 | 100 | 7.2 | Y |
| 31 | 11 (1.0) | 1 (0.01) | 1 (0.6) | 1 (4.84) + 2 (1.86) | 70 | 1 | 50.0 | 52 | 2.1 | Y |
| 32 | 6* (1.0) | 1 (0.003) | 1 (2.1) | 1 (1.39) + 2 (0.11) | 110 | 1 | 66.7 | 8 | 2.9 | Y |
| 33 | 6* (1.0) | 1 (0.003) | 2 (1.6) | 1 (1.5) | 110 | 6 | 0.0 | 0 | 0 | N |
| 34 | 6* (1.0) | 1 (0.003) | 1 (2.1) | 2 (1.5) | 70 | 2 | 36.7 | 100 | 19.8 | Y |
| 35 | 12 (1.0) | 1 (0.005) | 1 (2.1) | 2 (1.5) | 110 | 4 | 90.0 | 100 | 1440 | Y |
| 36 | 4* (1.0) | 1 (0.003) | 1 (1.6) | 2 (1.5) | 70 | 6 | 73.3 | 100 | N.D. | Y |
| 37 | 9* (1.0) | 1 (0.003) | 1 (2.1) | 1 (1.39) + 2 (0.11) | 110 | 3 | 0 | 0 | 0 | N |
| 38 | 8* (1.0) | 1 (0.003) | 1 (1.9) | 2 (1.5) | 110 | 3 | 0 | 0 | 0 | N |
| 39 | 10 (10.0) | None | 1 (0.17) | 2 (3.2) | 140 | 2 | 57 | 100 | 4250 | Y |
| 40 | 10 (1.0) | 1 (0.003) | None | 2 (1.5) | 110 | 4 | 0 | 0 | 0 | N |
| 41 | 1* (1.0) | None | 1 (0.6) | 1 (4.0) | 110 | 24 | 80 | 0 | 0 | Y |
| 42 | 2* (1.0) | 1 (0.003) | None | 2 (2.0) | 70 | 6 | 0.0 | 0 | 0 | N |
| 43 | 2* (1.0) | 5 (0.05) | None | 1 (1.5) + 2 (0.5) | 70 | 6 | 0.0 | 0 | 0 | N |
| 44 | 3* (1.0) | 5 (0.05) | None | 1 (1.5) + 2 (0.5) | 70 | 6 | 86.0 | 26 | 3.5 | Y |
| 45 | 14* (1.0) | 5 (0.05) | None | 1 (1.5) + 2 (0.5) | 70 | 6 | 80.0 | 16 | 3.0 | Y |
| 46 | 15 (1.0) | 1 (0.003) | 1 (4.3) | 1 (1.0) | 110 | 4 | 100 | 0 | 0 | Y |

*dried prior to use.
N.D. = Not Determined

Results

Table 2 reveals that xanthan gum (sample 37) and chitin (sample 38) did not successfully silylate. Table 2 further reveals a variety of polysaccharides that comprise fructose, galactose, anhydrogalactose, or glucose linked saccharide 33 mol % OH substitution in an absence of solvent, in aprotic solvent, or in non-polar solvents and that is unique among the polysaccharides. See, for example, the focused summary of results in Table 3. Other polysaccharides require a polar aprotic solvent.

TABLE 3

| Sample | Polysaccharide | Solvent | Catalyst | Reaction* (success/ failure) |
|---|---|---|---|---|
| 11 | beta-cyclodextrin (DP = 7) | Polar aprotic | 1 | Success |
| 9 | beta-cyclodextrin (DP = 7) | NONE | 1 | Success |
| 15 | beta-cyclodextrin (DP = 7) | Non-Polar | 1 | Success |
| 2 | beta-cyclodextrin (DP = 7) | Non-Polar | 1 | Success |
| 10 | beta-cyclodextrin (DP = 7) | Non-Polar | 1 | Success |
| 22 | Maltodextrin (DP = 17) | Polar Aprotic | 1 | Success |
| 21 | Maltodextrin (DP = 17) | NONE | 1 | Failure |
| 42 | Maltodextrin (DP = 17) | NONE | 5 | Failure |
| 19 | Maltodextrin (DP = 16-28) | Non-Polar | 1 | Failure |
| 43 | Maltodextrin (DP = 17) | NONE | 5 | Failure |
| 44 | Maltodextrin (DP = 4.3) | NONE | 5 | Success |
| 45 | Maltodextrin (DP = 7.3) | Non-Polar | 5 | Success |
| 32 | Inulin (DP = 18) | Polar Aprotic | 1 | Success |
| 33 | Inulin (DP = 18) | Non-Polar | 1 | Failure |
| 40 | Cellulose | Polar Aprotic | 1 | Success |
| 41 | Cellulose | None | 1 | Failure |

*Success means at least 33 mol % OH substitution

Test non-polar aromatic solvent solubility of select silylated polysaccharides using benzene as a representative solvent. Place 10 milligrams of silylated polysaccharide to 0.6 milliliters of benzene and heat to 80° C. for up to 8 hours to determine if the polysaccharide will dissolve. Table 4 shows the representative samples and the results of solubility test in benzene. Solubility results in Table 4 reveal that silylated polysaccharides of the present invention are soluble in benzene yet silylated starch and silylated cellulose is not soluble in benzene.

TABLE 4

| Sample | Polysaccharide | Soluble in Benzene? (Y/N) |
|---|---|---|
| 5 | beta-cyclodextrin | Y |
| 22, 24, 44 | Maltodextrin | Y |
| 26, 27 | Pullulan | Y |
| 28, 29 | Dextran | Y |
| 30, 31 | Trehalose | Y |
| 32, 33 | Inulin | Y |
| 35 | Agarose | Y |
| 36 | Starch | N |
| 39 | Cellulose | N |

Coloration in Subsequent Hydrosilylation

Test coloration in hydrosilylation by adding silylated polysaccharide, SiH Polymer and xylenes according to the amounts noted below to a 40-milliliter vial. Add a polytetrafluoroethylene stir bar and heat the mixture to 70° C. while mixing. Add 150 microliters of Platinum catalyst. Continue heating the reaction for 2.5 hours.

Evaluate four different reaction products using ASTM D1209-05 to determine the APHA color value for each. The four different reaction products and the APHA Color determination are as follows:

(1) Reference=use xylenes (0.92 milliliters) and SiH Polymer (0.35 g). Run just the SiH polymer through reaction conditions without a terminal alkenyl containing reactant. Resulting APHA color=>500

(2) Vinyl-free beta-cyclodextrin=use xylenes (0.92 milliliters), SiH Polymer (0.25 g) and Sample 41 (0.20 g) as the silylated polysaccharide, which is 80 mol % silylated but with fully saturated silyl groups. Resulting APHA color=>500

(3) 33 Mol % vinyl beta-cyclodextrin=use xylenes (0.92 milliliters), SiH Polymer (0.25 g) and Sample 17(0.20 g) as the silylated polysaccharide, with 70 mol % —OH substitution and 33 mol % vinyl substitution. Resulting APHA color=140.

(4) 100 Mol % vinyl beta-cyclodextrin=use xylenes (0.92 milliliters), SiH Polymer (0.36 g) and Sample 18 (0.09 g) as the silylated polysaccharide, which is a 75 mol % —OH substitution and 100 mol % vinyl substitution. Resulting APHA color=50.

Results reveal that vinyl-functional silylated beta-cyclodextrin surprisingly achieves an APHA color of less than 500, even less than 300 after being included in a hydrosilylation reaction with a platinum catalyst.

Hydrolytic Instability of C—O—Si Bond Versus C—O—C Bond

Samples (15 mg) were placed into a glass NMR tube in 0.6 mL of either d6-acetone (Sample 46) or d6-DMSO (Polysaccharide 15). Then, 5 µL of a 9:1 v/v solution of water/trifluoroacetic acid was added, and 1H NMR spectra were acquired at the timepoints in Table 5. The Mol % C—O—Si hydrolysis was measured by integrating TMS-cyclodextrin peaks from δ 0.1-0.3 ppm and hydrolyzed TMS groups from δ 0.03-0.07 ppm. The Mol % C—O—C hydrolysis was determined by evaluating C—O—CH$_3$ as determined by assessing growth of any resonances of MeOH, present at δ 3.31 in d6-acetone and δ 3.16 in d6-DMSO. After the 5 h time point for sample 46, a white precipitate was observed in the NMR tube. The precipitate was isolated by evaporating volatiles. The precipitate was soluble in d6-DMSO and analyzed to be consistent with the starting material, Polysaccharide 15.

TABLE 5

| Sample | Time (h) | Mol % C—O—Si Hydrolysis | Mol % —C—O—C Hydrolysis |
|---|---|---|---|
| 46 | 0 | 3 | 0 |
| 46 | 0.5 | 13 | 0 |
| 46 | 5 | 84 | 0 |
| Polysaccharide 15 | 0 | N/A | 0 |
| Polysaccharide 15 | 3 | N/A | 0 |

Sample 46 shows an increase in the amount of hydrolyzed C—O—Si bonds over time, increasing from 3% hydrolyzed at time 0 (due to residual byproduct from the synthesis reaction) to 84% hydrolyzed after 5 hours (h) at room temperature. The methyl groups from that sample forming C—O—C bond, however, remain intact and do not show any evidence of hydrolysis. As a control case, a pristine sample of methyl-beta-cyclodextrin was also treated with trifluoroacetic acid as above. This sample also did not show any degradation of the C—O—C groups after 3 h at room temperature demonstrating the stability of this bond.

Hence, the data affirms a lower hydrolytic stability of C—O—Si bonds relative to the C—O—C bonds.

What is claimed is:

1. A composition comprising a silylated polysaccharide, where the silylated polysaccharide is characterized by:
   a. comprising linked fructose, galactose, anhydrogalactose, or glucose saccharide units provided that glycosidic linkages of glucose are alpha linkages and that the silylated polysaccharide is other than a silylated starch; and
   b. on average 1 to 100 mole-percent of the hydroxyl groups on the polysaccharide have been silylated with a silyl group having the structure —SiR$_3$ linked to the polysaccharide through a C—O—Si bond where each R is independently selected from hydrocarbyl radicals having from one to 12 carbon atoms, provided that on average at least one R per polysaccharide has a terminally unsaturated carbon-carbon double bond.

2. The composition of claim 1, wherein the silylated polysaccharide is selected from a group consisting of silylated beta-cyclodextrin, silylated maltodextrin, silylated pullulan, silylated dextran, silylated trehalose, silylated sucrose, silylated lactose, silylated maltose, silylated inulin, and silylated agarose.

3. The composition of claim 1, wherein the silylated polysaccharide comprises on average 2 to 2000 saccharide units per molecule.

4. The composition of claim 1, wherein at least two R groups per silylated polysaccharide has a terminally unsaturated carbon-carbon double bond.

5. The composition of claim 1, wherein each R is selected from methyl and vinyl groups.

6. A method for preparing the silylated polysaccharide of claim 1, the method comprising the steps:
  a. providing a polysaccharide comprising fructose, galactose, anhydrogalactose, or glucose linked saccharide units provided that glycosidic linkages of glucose are alpha linkages and that the silylated polysaccharide is other than a silylated starch; and
  b. silylating on average 1 to 100 mole-percent of the hydroxyl groups on the polysaccharide by substituting the hydrogen atom of the hydroxyl group with a group having the formula: —$SiR_3$ where R is independently selected from hydrocarbyl radicals having from one to 12 carbon atoms, provided that on average at least one R per polysaccharide is a terminal alkenyl group.

7. The method of claim 6, wherein the polysaccharide has an average degree of polymerization that is less than or equal to 8 and wherein silylation occurs in an absence of polar aprotic solvent.

8. The method of claim 6, wherein the silylation occurs by reacting the polysaccharide with 1,1,3,3-tetraalkyl-1,3 divinyldisilazane and optionally hexaalkyldisilazane.

9. The method of claim 6, wherein the polysaccharide is selected from a group consisting of beta-cyclodextrin, maltodextrin, pullulan, dextran, trehalose, sucrose, lactose, maltose, inulin, and agarose.

10. The method of claim 6, where each R is selected from methyl and vinyl groups.

* * * * *